United States Patent [19]

Tabak

[11] Patent Number: 4,547,602

[45] Date of Patent: * Oct. 15, 1985

[54] REACTOR SEQUENCING SYSTEM FOR CONVERTING OXYGENATES TO HYDROCARBONS

[75] Inventor: Samuel A. Tabak, Wenonah, N.J.

[73] Assignee: Mobil Oil Corporation, New York, N.Y.

[ * ] Notice: The portion of the term of this patent subsequent to Nov. 13, 2001 has been disclaimed.

[21] Appl. No.: 645,137

[22] Filed: Aug. 28, 1984

Related U.S. Application Data

[63] Continuation-in-part of Ser. No. 548,377, Nov. 3, 1983, Pat. No. 4,482,772, and Ser. No. 526,852, Aug. 26, 1983, Pat. No. 4,487,985.

[51] Int. Cl.⁴ ............................. C07C 5/00; C07C 1/00
[52] U.S. Cl. ..................................... 585/314; 585/254; 585/255; 585/315; 585/330
[58] Field of Search ............... 585/254, 255, 314, 315, 585/330

[56] References Cited

U.S. PATENT DOCUMENTS 4,401,558  8/1983  Pellet et al. ........................ 585/324
4,482,772  11/1984  Tabak ................................. 585/254

Primary Examiner—Curtis R. Davis
Attorney, Agent, or Firm—A. J. McKillop; M. G. Gilman; L. G. Wise

[57] ABSTRACT

An integrated process is provided for converting methanol or the like to heavy hydrocarbon products, especially distillate range hydrocarbons. In a first stage catalytic process oxygenate feedstock is converted to lower olefins, which are passed through a second stage oligomerization reactor. A reactor sequencing technique is useful for multi-stage catalytic conversion systems employing a number of fixed bed catalytic reactors at various process temperatures and catalytic activity levels.

11 Claims, 4 Drawing Figures

REACTOR SEQUENCING SYSTEM FOR CONVERTING OXYGENATES TO HYDROCARBONS

REFERENCE TO COPENDING APPLICATION

This application is a continuation-in-part of U.S. patent applications Ser. No. 548,377, filed Nov. 3, 1983, now U.S. Pat. No. 4,482,772 and Ser. No. 526,852, filed Aug. 26, 1983, now U.S. Pat. No. 4,487,985 incorporated herein by reference.

BACKGROUND OF THE INVENTION

This invention relates to an integrated system for converting oxygenates, such as methanol or dimethyl ether (DME), to liquid hydrocarbons. In particular it provides a continuous process for converting the oxygenate feedstock catalytically to produce an intermediate lower olefinic stream and oligomerizing the olefins to produce distillate/gasoline or similar heavy hydrocarbons.

Recent developments in zeolite catalysts and hydrocarbon conversion processes have created interest in utilizing olefinic feedstocks, for producing $C_5^+$ gasoline, diesel fuel, etc. In addition to the basic work derived from ZSM-5 type zeolite catalysts, a number of discoveries have contributed to the development of a new industrial process, known as Mobil Olefins to Gasoline/Distillate ("MOGD"). This process has significance as a safe, environmentally acceptable technique for utilizing feedstocks that contain lower olefins, especially $C_2$-$C_5$ alkenes. This process may supplant conventional alkylation units. In U.S. Pat. Nos. 3,960,978 and 4,021,502, Plank, Rosinski and Givens disclose conversion of $C_2$-$C_5$ olefins, alone or in admixture with paraffinic components, into higher hydrocarbons over crystalline zeolites having controlled acidity. Garwood et al have also contributed improved processing techniques to the MOGD system, as in U.S. Pat. Nos. 4,150,062, 4,211,640 and 4,227,992. The above-identified disclosures are incorporated herein by reference.

Conversion of lower olefins, especially propene and butenes, over HZSM-5 is effective at moderately elevated temperatures and pressures. The conversion products are sought as liquid fuels, especially the $C_5^+$ aliphatic and aromatic hydrocarbons. Olefinic gasoline is produced in good yield by the MOGD process and may be recovered as a product or recycled to the reactor system for further conversion to distillate-range products. Operating details for typical MOGD units are disclosed in U.S. Pat. Nos. 4,456,779 (Owen et al) and 4,433,185 (Tabak), incorporated herein by reference.

In addition to their use as shape selective oligomerization catalysts, the medium pore ZSM-5 type catalysts are useful for converting methanol and other lower aliphatic alcohols or corresponding ethers to olefins. Particular interest has been directed to a catalytic process for converting low cost methanol to valuable hydrocarbons rich in ethene and $C_3^+$ alkenes. Various processes are described in U.S. Pat. Nos. 3,894,107 (Butter et al), 3,928,483 (Chang et al), 4,025,571 (Lago), and in copending U.S. patent application Ser. No. 516,234, filed July 22, 1983 (Yurchak et al). Significance of the methanol-to-olefins ("MTO") type processes, especially for producing ethene, is discusssed in *Hydrocarbon Processing*, November 1982, pp. 117–120. It is generally known that the MTO process can be optimized to produce a major fraction of $C_2$-$C_4$ olefins; however, a significant $C_5^+$ byproduct is coproduced, including polymethylbenzenes, such as durene, as described in U.S. Pat. No. 4,025,576 (Chang et al). Prior process proposals have included a separation section to recover ethene and other gases from byproduct water and $C_5^+$ hydrocarbon liquids. Treatment of the $C_5^+$ liquids to dealkylate the polymethylbenzenes has been necessary to convert this fraction to satisfactory liquid fuel, for instance as disclosed in U.S. Pat. Nos. 4,347,397 (Dwyer et al) and 4,387,261 (Chester et al). Such post treatment processes add significantly to the cost of liquid fuels plant.

SUMMARY OF THE INVENTION

It has been discovered that methanol, DME or the like may be converted to liquid fuels, particularly distillate, in a multi-stage continuous process, with integration between the major process units. In an integrated continuous process for converting oxygenated organic feedstock to liquid hydrocarbons including the steps of (a) contacting feedstock with at least one primary stage fixed bed reactor containing acidic zeolite catalyst at elevated temperature and moderate pressure to convert at least a portion of the feedstock to hydrocarbons containing a major fraction of $C_2$-$C_4$ olefins; (b) cooling and separating primary stage effluent to recover a light hydrocarbon vapor stream rich in $C_2$-$C_4$ olefins; (c) pressurizing and heating at least a portion of the olefinic light hydrocarbon stream to form a secondary stage olefinic feedstream; (d) contacting the olefinic feedstream in a secondary stage comprising a plurality of serially connected fixed bed reactors containing medium-pore shape selective acidic zeolite catalyst under oligomerization/polymerization conditions at substantially increased pressure and moderate temperature to convert olefins to a heavier liquid hydrocarbon effluent stream; the improvement herein comprises: a cyclic fluid handling technique to connect the secondary stage serial reactors in operative fluid flow relationship whereby fresh or regenerated catalyst in a terminal reactor stage position receives effluent from at least one preceding secondary stage reactor operating at moderate temperature, said preceding secondary stage reactor containing catalyst of less activity than said catalyst in the terminal reactor stage position; sequencing process flow to connect said preceding secondary stage reactor in said primary stage for receiving an oxygenated feedstock; increasing temperature in the previously preceding secondary stage reactor to primary stage temperature conditions; removing a primary stage reactor containing inactivated catalyst from conversion service; connecting the reactor containing inactivated catalyst in fluid flow relationship with a catalyst regeneration loop; regenerating said catalyst in situ; advancing the terminal reactor of the secondary stage to a preceding serial position in the secondary stage; and adding a fresh or regenerated catalyst reactor in the secondary stage terminal position.

Other objects and features of the invention will be seen in the following description and drawings.

THE DRAWINGS

DESCRIPTION OF PREFERRED EMBODIMENTS

Figure 1:
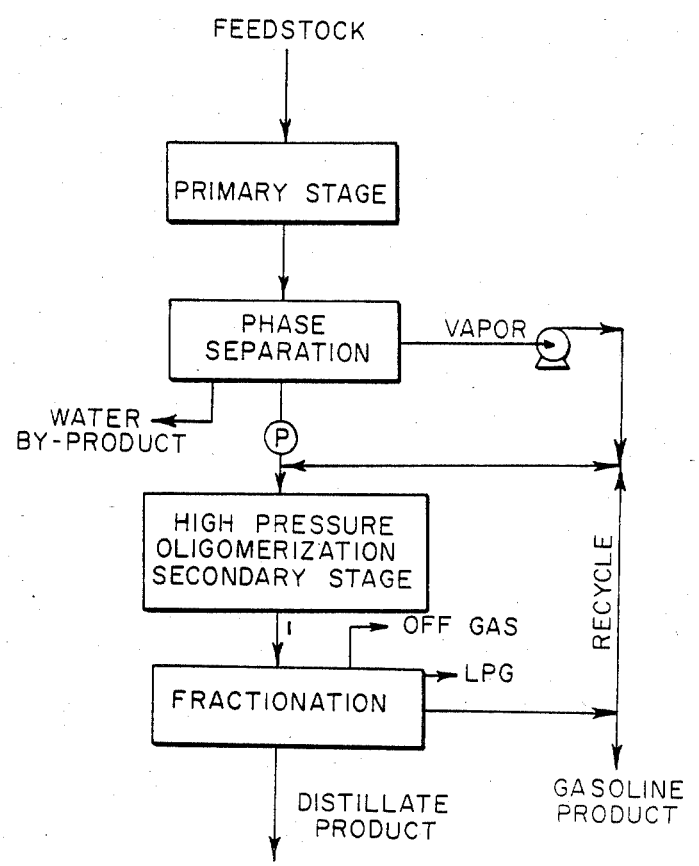
FIG. 1 is a process flow sheet showing the major unit operations and process streams.

The present invention takes advantage of the accelerated aging rate for hydrocarbon conversion catalysts operating under process conditions which produce coke deposits. Increased coking will decrease conversion at a given temperature, and it is conventional practice to increase process temperature to maintain the desired level of conversion. In the two stage conversion process contemplated in the preferred embodiment herein, the primary stage effluent is selectively converted in a secondary stage over highly active ZSM-5 type catalyst at moderate temperature and high pressure. Under these conditions $C_3+$ olefin primary reactants are converted efficiently in major amount to a highly desirable distillate product or the like. The primary stage advantageously can utilize coked catalyst that would no longer be suitable for lower temperature use due to loss of activity. In order to maintain the MOGD plant in continuous operation, it is necessary to either replace or regenerate spent catalyst periodically. A single reactor can serve different functions in the multi-stage complex by appropriate sequencing of a plurality of fixed bed reactors. By employing the same type of catalyst bed in similar amount and configuration for each reactor, the same reactor shell can be switched to serve in any of the process positions according to need.

Catalyst versatility permits the same zeolite to be used in both the primary dehydration stage (MTO) and secondary oligomerization stage (MOGD). It is advantageous to employ a standard ZSM-5 having a silica:alumina molar ratio of 70:1.

The oligomerization catalysts preferred for use herein include the crystalline aluminosilicate zeolites having a silica to alumina ratio of at least 12, a constraint index of about 1 to 12 and acid cracking activity of about 160-200. Representative of the ZSM-5 type zeolites are ZSM-5, ZSM-11, ZSM-12, ZSM-22, ZSM-23, ZSM-35 and ZSM-38. ZSM-5 is disclosed and claims in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosures of these patents are incorporated herein by reference. A suitable catalyst for fixed bed operation is HZSM-5 zeolite with 35 wt. % alumina binder in the form of cyclindrical extrudates of about 1-5 mm.

These medium pore shape selective catalysts are sometimes known as porotectosilicates or "Pentasil" catalysts. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and oligomerization.

In this description, metric units and parts by weight are employed unless otherwise stated. While various reactor configurations may be used, including fluidized bed catalytic reactors, moving bed and fixed bed reactors, the invention is described for use in a plurality of fixed bed reactors operated under differing process conditions depending upon relative position in the system.

Referring to FIG. 1, the process feedstock (methanol or DME, for instance) is fed to the primary stage where it is converted to a lower olefin and gasoline hydrocarbon plus water by dehydration of the oxygenated feedstock. Byproduct water is recovered by simple phase separation from the cooled effluent. Liquid hydrocarbons consisting essentially of $C_5+$ gasoline range materials are pumped to the higher secondary stage pressure. This stream may contain as much as 6 to 10 wt. % durene. At least a portion of the vapor phase effluent from the primary stage is compressed and heated along with the liquids to oligomerization reaction temperature, and the combined olefinic stream (optionally containing recycled olefinic gasoline) is reacted at high pressure and elevated temperature over the catalyst. Secondary stage effluent is then separated into light gases, $C_5+$ gasoline for recycle in part and distillate range hydrocarbons. The distillate stream contains a major fraction of high boiling aliphatics and a minor amount of aromatics. Hydrotreating (HDT) in the final stage is a relatively mild process to saturate the olefinic compounds and convert the aromatics to corresponding naphthenes without substantial cracking or dealkylation to yield a distillate fuel product. Ethylene (ethene, $C_2H_2$) may be recovered as a valuable chemical feedstock from the process.

In the process for catalytic conversion of olefins to heavier hydrocarbons by catalytic oligomerization using an acid crystalline zeolite, such as ZSM-5 type catalyst, process conditions can be varied to favor the formation of either gasoline or distillate range products. At moderate temperature and relatively high pressure, the conversion conditions favor distillate range product having a normal boiling point of at least 165° C. (330° F.). Lower olefinic feedstocks containing $C_2-C_6$ alkenes may be converted selectively; however, the distillate mode conditions do not convert a major fraction of ethylene. While propene, butene-1 and others may be converted to the extent of 50 to 95% in the distillate mode, only about 10 to 50% of the ethylene component will be consumed. Accordingly, the ethene is advantageously recovered prior to the secondary oligomerization stage, as shown in FIG. 2, which depicts a preferred system for converting methanol ($CH_3OH$) and/or DME.

In the primary stage ethene production may be optimized by employing fixed bed primary stage conditions in the temperature range of about 260° C. to 425° C., a pressure range of about 170 to 800 kPa and weight hourly space velocity range of about 0.5 to 1.0 based on ZSM-5 equivalent catalyst and methanol equivalent in the primary stage feedstock. Typically about 25 to 90% of MeOH/DME feedstock is converted per reactor pass and water diluent is cofed with methanol and/or dimethyl ether in a molar ratio of about 0.1:1 to 5:1. Under these conditions, the primary stage hydrocarbon effluent usually contains about 25 to 40 wt. % ethene, about 10 to 50 wt. % propene, about 2 to 30 wt. % butene, less than 10 wt. % $C_1$ to $C_4$ paraffins, and about 5 to 20 wt. % aromatics, including about 1 to 5 wt. % durene.

Figure 2:
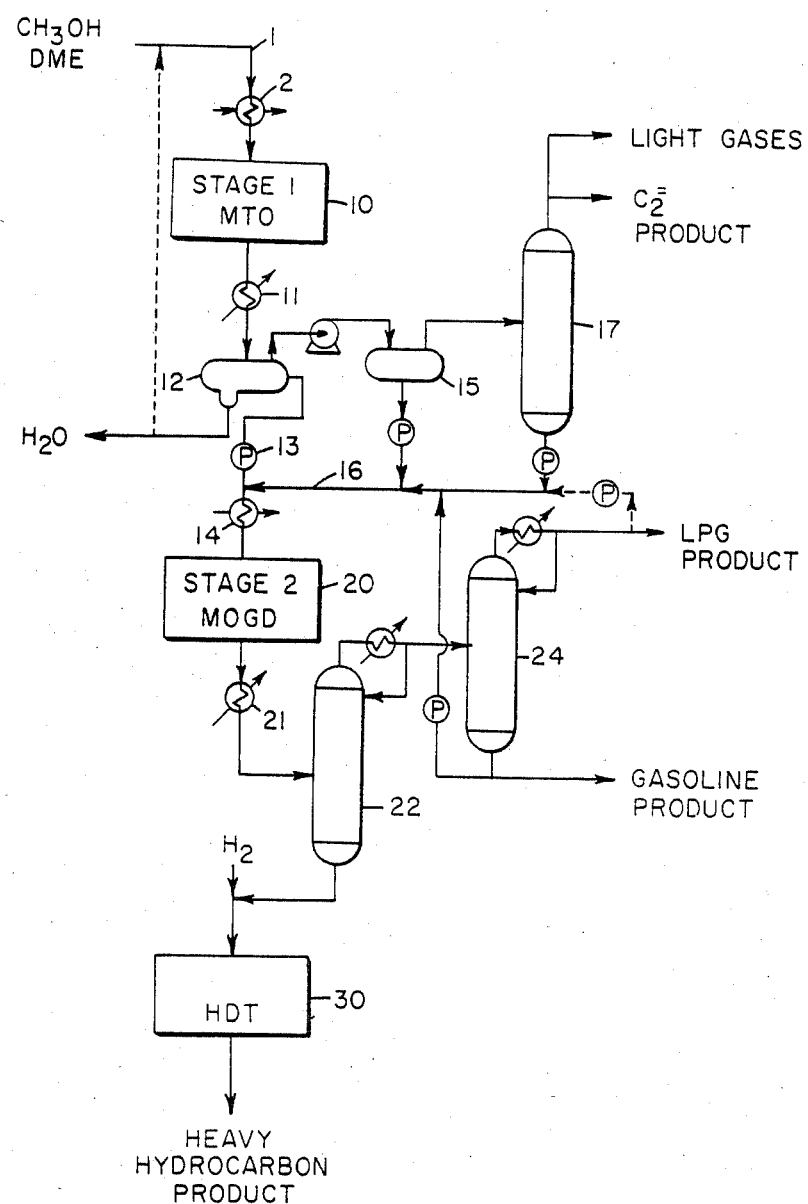
FIG. 2 is a schematic representation of a preferred multi-stage reactor system and fractionation system for ethane recovery.

In the preferred embodiment of FIG. 2, the feedstock is methanol, which may be partially dehydrated in a separate process step over gamma-alumina catalyst to yield dimethyl ether (DME) and water. A preliminary dewatering step can be used to provide a feedstock consisting essentially of $CH_3OH$ and/or DME; however, the presence of water in the MTO reactor may be beneficial. The feedstock is fed continuously under low pressure through line 1, and heat exchange 2 where it is raised to process temperature and introduced to the first stage MTO reactor system 10. The first stage effluent is cooled in exchanger 11 to condense water and a major amount of $C_5+$ hydrocarbons. These liquids are separated from the hydrocarbon vapor in phase separator means 12. Byproduct water may be recovered from unreacted feedstock and discarded or a portion may be recycled.

The liquid hydrocarbon phase from separator 12 is then brought up to distillate mode oligomerization pressure by pump 13, heated in exchanger 14 and introduced to the secondary stage reactor system 20. The ethene-rich hydrocarbon vapor stream from separator 12 is compressed and condensed liquid, mainly $C_3$–$C_4$ olefin, is separated in high pressure separator 15, after which it is pumped to secondary stage pressure and combined through conduit 16 with other hydrocarbon liquids. Ethene product and other $C_2-$ light gases are recovered from the vapor stream by fractionator unit 17, which may be a cryogenic still or the like. Methane and ethane offgas may be removed from the system at this point.

Pressurized $C_3+$ hydrocarbons from fractionator 17 are combined with other hydrocarbon liquid streams through conduit 16 and passed to the second stage MOGD reactor system 20 under high pressure at moderate temperature. As discussed hereafter, the preferred MOGD reactor system is a multizone arrangement. Second stage effluent is cooled in heat exchanger 21 and fractionated in distillation tower 22, from which the distillate range liquids boiling above about 165° to 175° C. (330° F.) are fed as a continuous stream to the third stage HDT reactor 30. Gasoline, rich in $C_5+$ olefins and lighter hydrocarbons are further fractionated in tower 24 to provide an olefinic gasoline stream for recycle to the MOGD reactor system or recovered as product. The lighter hydrocarbons, rich in $C_3$–$C_4$ alkenes may be condensed and recovered as LPG product or optionally recycled to the MOGD reactor system.

The main concept is to cascade substantially all $C_3+$ hydrocarbon first stage product into an MOGD reactor followed by hydrotreating of the distillate product. This will minimize the number of process steps and will maximize distillate production by polymerizing gasoline range olefins, and by alkylating gasoline range aromatics. Durene will be reduced via saturation to its corresponding naphthene in the hydrotreating step.

A typical MTO operation is conducted over a fixed bed of HZSM-5/alumina extrudate catalyst at about 170 kPa (25 psia), with a 1:1 $H_2O:CH_3OH$ equivalent ratio at 315° C. (600° F.) at a space velocity (WHSV=0.5-1) to convert about 50% of the oxygenated organic feedstock components to hydrocarbons. Table A lists the organic product distribution from a typical MTO run at 600° F.

TABLE A

| MTO Product Distribution | |
|---|---|
| Component | wt. % |
| Methane | 0.6 |
| Ethylene | 26.2 |
| Ethane | 0.1 |
| Propylene, wt. % | 22.8 |
| Propane | 3.9 |
| Butenes | 7.9 |
| Isobutane | 3.9 |
| n-Butane | 2.6 |
| Pentenes | 2.4 |
| $C_5$ P + N | 7.1 |
| $C_6$ P + N | 5.1 |
| $C_7$ O | 0.6 |
| $C_7$ P + N | 3.2 |
| $C_7$ O | 0.7 |
| $C_8$ P + O + N | 2.1 |
| $C_9$ P + O + N | 1.3 |
| $C_{10}$ P + O + N | 1.1 |
| Benzene | 0.1 |
| Toluene | 0.5 |
| $C_8$ Aromatics | 3.5 |
| $C_9$ Aromatics | 2.1 |
| $C_{10}$ Aromatics | 2.2 |
| Durene | 1.7 |

Figure 3:
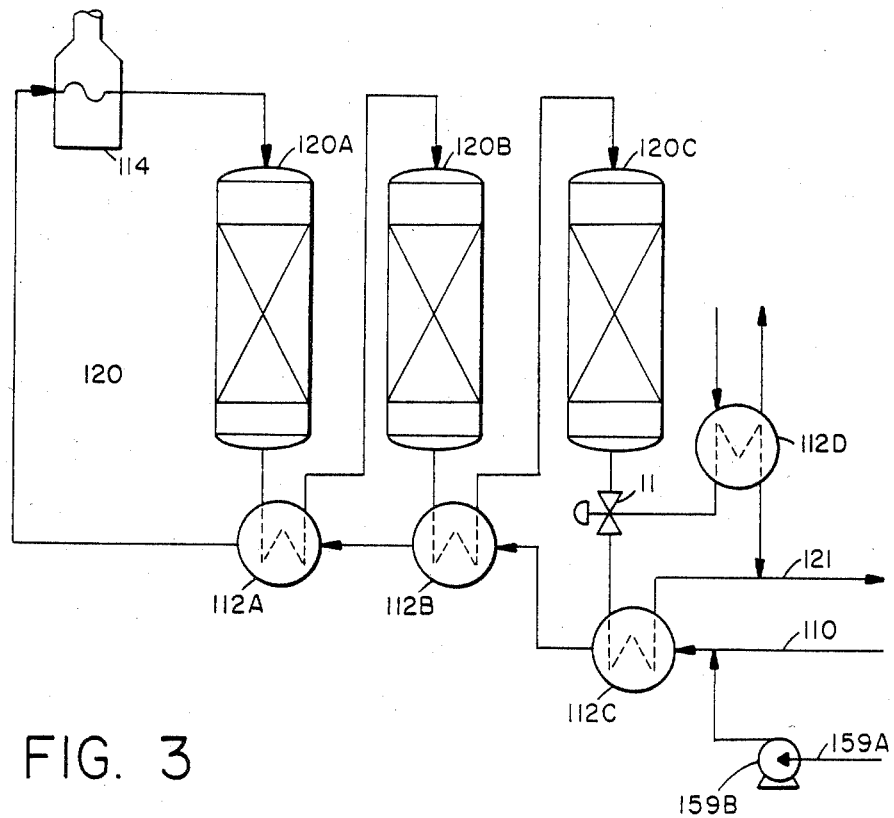
FIG. 3 depicts a typical olefin conversion reactor system for distillate mode operation.

A typical distillate mode secondary stage reactor system 120 is shown in FIG. 3. A plural reactor system may be employed with inter-reactor cooling, whereby the reaction exotherm can be carefully controlled to prevent excessive temperature above the normal moderate range of about 190° to 315° (375°-600° F.). The olefinic feedstream is introduced through conduit 110 and carried by a series of conduits through heat exchangers 112A, B, C and furnace 114 where the feedstream is heated to reaction temperature. The olefinic feedstock is then carried sequentially through a series of zeolite beds 120A, B, C wherein at least a portion of the olefin content is converted to heavier distillate constituents. Advantageously, the maximum temperature differential across only one reactor is about 30° C. ($\Delta T \sim 50°$ F.) and the space velocity (LHSV based on olefin feed) is about 0.5 to 1.5. The heat exchangers 112A and 112B provide inter-reactor cooling and 112C reduces the effluent to separation temperature. An optional heat exchanger 112D may further recover heat from the effluent stream 121 prior to separation. Gasoline from recycle conduit 159A is pressurized by pump means 159B and combined with the feedstream, preferably at a ratio of about 1-3 parts by weight per part of olefin in the secondary stage feedstream.

Preferably, the secondary stage process conditions are optimized to produce heavy liquid hydrocarbons having a normal boiling point greater than about 175° C., and employs a fixed bed of ZSM-5 type catalyst to oligomerize olefins at a start of cycle temperature of about 230° C. to 260° C. and pressure of about 4200 to 7000 kPa.

Rather than recover ethene and other light gases from the first stage effluent, ethene can be sent to the MOGD, it will pass through relatively unreacted, thus reducing the amount of $C_3+$ in the ethylene separation plant and improving its efficiency.

REACTOR SEQUENCING

Figure 4:
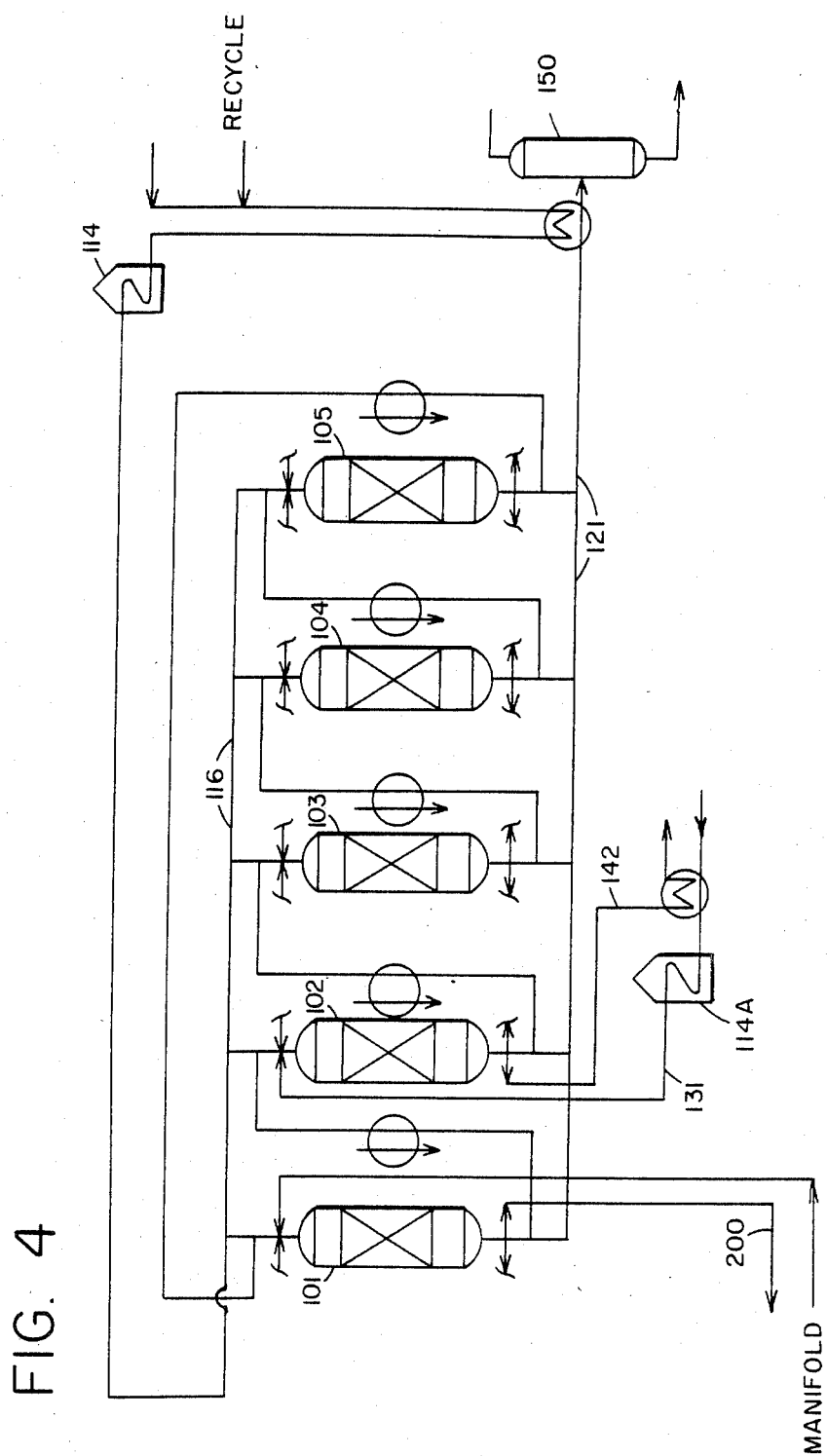
FIG. 4 depicts a typical reactor manifold system for multistage sequencing.

For sequencing catalyst beds, the most aged catalyst can be used in the high temperature reactor of the primary stage prior to regeneration. The advantage of rotating reactors through both stages over a conventional design is the need for only one spare reactor and only one regeneration loop. The multiple reactor configuration shown in FIG. 4 is operatively interconnected via fluid handling means to permit any of the five fixed substantially identical reactors to be placed in service for primary or secondary stage operation or regeneration according to the degree of catalyst coking. A number of reactors 101, 102, 103, 104, 105 are each connectable through suitable valving to olefin feed manifold 116, secondary stage effluent manifold 121, primary feed stream 131, primary stage effluent outlet 142, and regeneration manifold 200. FIG. 4 depicts a preferred two-stage plant to show a possible flow configuration for this system. Because of the large number of valves required, these have not been included in the drawings. However, it is understood that all lines require conventional multiple block valves for safety in handling both hydrocarbons and air.

In a five-reactor system—A,B,C,D,E,—for the initial cycle described, the feedstock is transported in sequence through reactors A, B, C, (Stage II) and reactor D (Stage I), while reactor E is out of service. The reactors are shifted in sequence as tabulated below.

| Cycle # | Secondary Stage | | | Primary Stage | Regen. |
| --- | --- | --- | --- | --- | --- |
| | First | Intermediate | Last | | |
| 1 | A | B | C | D | E |
| 2 | B | C | E | A | D |
| 3 | C | E | D | B | A |
| 4 | E | D | A | C | B |
| 5 | D | A | B | E | C |
| Repeat | A | B | C | D | E |

REGENERATION OPERATION

Preferably the ZSM-5 catalyst is kept on stream until the coke content increases from 0% at the start of cycle (SOC) until it reaches a maximum of 30 weight % at end of cycle (EOC) at which time it is regenerated by oxidation of the coke deposits. Typically a greater than 30-day total cycle can be expected between regenerations. The reaction operating temperature depends upon its serial position. The system is operated advantageously by increasing the operating temperature of the first reactor (Position A) from about 250° C.–290° C. (SOC) to about 270° C.–310° C. (EOC) at a catalyst aging rate of 1°–6° C./day. Secondary stage reactors in the second and subsequent positions (B, C, etc.), containing catalyst with less time in stream (i.e. higher catalytic activity, are operated at lower SOC temperature. Operating in such a manner the average reactor temperature for the reactor in position C will generally be less than the average reactor temperature in position B, which will generally be less than the average reactor temperature in position A. Thermodynamically it is advantageous to maintain the secondary stage terminal reactor (position C) with fresh catalyst, since this allows a lower average reactor temperature, which will form the product of higher molecular weight oligomer. The aging rate for reactors in positions B and C is about 1°–6° C./day. Aging rates for reactors in all secondary stage positions (A, B and C) are adjusted to maintain approximately equal conversion rates. The secondary stage end of cycle is signalled when the outlet temperature of the reactor in position A reaches its allowable maximum. At this time the inlet temperature is reduced to start of cycle levels in order to avoid excessive coking over the freshly regenerated catalyst when the regenerated reactor is brought on-line, after having been brought up to reaction pressure with an effluent slip stream. Regeneration of coked catalyst may be effected by any of several procedures. The catalyst may be removed from the reactor of the regeneration treatment to remove carbonaceous deposits or the catalyst may be regenerated in-situ in the reactor. A programmable logic controller may be employed to control the sequencing of valve operations during all stages of reactor system operation.

As compared to a conventional system wherein MTO liquids containing gasoline range materials and durene are recovered and severely hydrotreated to reduce the durene content by dealkylation, the present system is an economic process for increasing the relative amount of distillate. Typically, an increase of 40% or more of high quality fuel can be achieved. The amount of aromatics in the gasoline is likewise decreased from about 22% to 15%. The preferred distillate mode operation can provide a larger part of the total fuel products as heavy hydrocarbons, usually in a distillate/gasoline ratio of about 1.3 to 6:1, while retaining a high yield of valuable ethylene product. Substantially all of the polymethylbenzenes or other aromatics formed in the dehydration reactor stage are accumulated in the distillate fraction according to the present invention, and the hydrotreated distillate durene content is decreased substantially below 2 wt. %, preferably below 1%.

The present process is particularly useful in producing a major product stream wherein the 175° C.+ fraction consists mainly of $C_{10}$ to $C_{20}$ aliphatic hydrocarbons containing a minor amount of cyclic components. The low temperature, high pressure distillate mode secondary stage operation favors the formation of linear oligomers.

By integration of dehydration, oligomerization and hydrotreating, a route is provide for converting MTC products to distillate with a minimum of processing steps. This technique will reduce capital cost and provide an economic process for production of distillate fuels and ethene, with gasoline and LPG being made in minor amount.

Various modifications can be made to the system, especially in the choice of equipment and non-critical processing steps. While the invention has been described by specific examples, there is no intent to limit the inventive concept as set forth in the following claims.

I claim:

1. In an integrated continuous process for converting oxygenated organic feedstock to liquid hydrocarbons including the steps of
    (a) contacting feedstock with at least one primary stage fixed bed reactor containing acidic zeolite catalyst at elevated temperature and moderate pressure to convert at least a portion of the feedstock to hydrocarbons containing a major fracton of $C_2$–$C_4$ olefins;
    (b) cooling and separating primary stage effluent to recover a light hydrocarbon vapor stream rich in $C_2$–$C_4$ olefins;
    (c) pressurizing and heating at least a portion of the olefinic light hydrocarbon stream to form a secondary stage olefinic feedstream;
    (d) contacting the olefinic feedstream in a secondary stage comprising a plurality of serially connected fixed bed reactors containing medium-pore shape selective acidic zeolite catalyst under oligomerization/polymerization conditions at substantially increased pressure and moderate temperature to convert olefins to a heavier liquid hydrocarbon effluent stream;

the improvement which comprises:

a cyclic fluid handling technique to connect the secondary stage serial reactors in operative fluid flow relationship whereby fresh or regenerated catalyst in a terminal reactor stage position receives effluent from at least one preceding secondary stage reactor operating at moderate temperature, said preceding secondary stage reactor containing catalyst of less activity than said catalyst in the terminal reactor stage position;

sequencing process flow to connect said preceding secondary stage reactor in said primary stage to receive said oxygenated feedstock;

increasing temperature in said previously preceding secondary stage reactor to primary stage temperature conditions;

removing a primary stage reactor containing inactivated catalyst from conversion service;

connecting the reactor containing inactivated catalyst in fluid flow relationship with a catalyst regeneration loop;

regenerating said catalyst in situ;

advancing the terminal reactor of the secondary stage to a preceding serial position in the secondary stage; and adding a fresh or regenerated catalyst reactor in the secondary stage terminal position.

2. The process of claim 1 wherein the primary and secondary stage reactor zones contain an acid ZSM-5 type catalyst.

3. The process of claim 2 comprising fixed bed down flow pressurized reactors having a porous bed of ZSM-5 type catalyst particles with an acid activity of about 160 to 200, based on fresh catalyst.

4. The process of claim 1 wherein primary stage feedstock comprising methanol and/or dimethyl ether is converted over HZSM-5 type catalyst to hydrocarbons comprising a major amount of $C_2$-$C_4$ olefins and a minor amount of normally liquid hydrocarbons containing durene.

5. The process of claim 4 wherein ethene production is optimized by employing fixed bed primary stage conditions in the temperature range of about 260° C. to 425° C., a pressure range of about 170 to 800 kPa and weight hourly space velocity range of about 0.5 to 1.0 based on ZSM-5 equivalent catalyst and methanol equivalent in the primary stage feedstock.

6. The process of claim 5 wherein primary stage hydrocarbon effluent contains about 5 to 40 wt. % ethene, about 10 to 60 wt % propene about 2 to 30 wt. % butene, less than 10 wt. % $C_1$ to $C_4$ paraffins, about 5 to 20 wt. % aromatics, including about 1 to 5 wt. % durene.

7. The process of claim 4 wherein ethene is recovered from the primary stage effluent by fractionation.

8. The process of claim 1 wherein the primary stage effluent is cooled under process pressure and light hydrocarbon vapors are compressed to form a second liquid hydrocarbon stream to be fed under process pressure to the secondary stage.

9. The process of claim 8 wherein compressed light hydrocarbon vapor is fractionated to recover an ethene-rich product stream.

10. A multistage process for converting oxygenate feedstock comprising methanol, dimethylether or mixtures thereof to liquid hydrocarbon product utilizing a regenerable acid zeolite catalyst in a plurality separately operable catalytic reactor units; advancing fresh or regenerated catalyst from a terminal position wherein relatively active catalyst oligomerizes olefinic intermediates to heavier hydrocarbon product toward an initial oligomerization unit utilizing less active catalyst than the terminal position unit;

further advancing catalyst from the initial oligomerization unit to a primary conversion unit wherein oxygenate feedstock is converted to lower olefins;

operating the primary stage conversion unit with relatively inactive catalyst at conversion temperature substantially higher than the initial oligomerization unit and terminal unit;

periodically removing spent catalyst from the primary conversion unit;

regenerating the spent catalyst to restore acid activity; and advancing at least a portion of the regenerated catalyst to the terminal position unit for further service at relatively low oligomerization temperature.

11. The process of claim 10 wherein spent catalyst removed from the primary conversion unit contains about 10 to 30 wt. % coke.

* * * * *